US010046278B2

(12) United States Patent
Kusters et al.

(10) Patent No.: US 10,046,278 B2
(45) Date of Patent: Aug. 14, 2018

(54) METHOD FOR CONTROLLING FOULING DURING A SPINNING MEMBRANE FILTRATION PROCEDURE

(71) Applicant: Fenwal, Inc., Lake Zurich, IL (US)

(72) Inventors: Benjamin E. Kusters, Pleasant Prairie, WI (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 15/482,248

(22) Filed: Apr. 7, 2017

(65) Prior Publication Data

US 2017/0326502 A1 Nov. 16, 2017

Related U.S. Application Data

(60) Provisional application No. 62/334,249, filed on May 10, 2016.

(51) Int. Cl.
*A61M 1/34* (2006.01)
*B01D 63/16* (2006.01)
(Continued)

(52) U.S. Cl.
CPC ........... *B01D 65/08* (2013.01); *A61M 1/3496* (2013.01); *B01D 63/16* (2013.01); *C12N 5/0641* (2013.01);
(Continued)

(58) Field of Classification Search
CPC ........ B01D 65/08; B01D 63/06; B01D 63/16; B01D 2315/02; B01D 2321/00;
(Continued)

(56) References Cited

U.S. PATENT DOCUMENTS 4,828,543 A * 5/1989 Weiss ...................... A61M 1/16
210/637
4,879,040 A * 11/1989 Prince ..................... A61M 1/34
210/637
(Continued)

FOREIGN PATENT DOCUMENTS

EP          0310205 A2    4/1989
JP          200982029 A   4/2009

OTHER PUBLICATIONS

European Patent Office, Extended European Search Report, counterpart EP Appl. No. 17169240, dated Sep. 9, 2017.

*Primary Examiner* — Joseph W Drodge
(74) *Attorney, Agent, or Firm* — Cook Alex Ltd.

(57) ABSTRACT

Methods for controlling a spinning membrane separator so as to limit fouling of the membrane by changing the rotation rate of the spinning membrane in response to the fouling rate, while maintaining a constant outlet cellular concentration. Increasing the spinner rotation rate will increase the strength of the Taylor vortices generated within the separator by the spinning of the membrane, which should reduce fouling of the membrane. The goal of the method is to rotate the spinning membrane at the slowest rate possible without unacceptable fouling. Two specific methods to control fouling are disclosed. In a first, unidirectional method, the spin rate of the membrane is only increased in response to undesirable fouling in order to prevent the fouling from continuing. In a second, bidirectional method, the spin rate of the membrane may be either increased or decreased in response to the measured fouling rate in order to maintain the fouling rate within a desired range.

12 Claims, 5 Drawing Sheets

(51) Int. Cl.
*B01D 65/08* (2006.01)
*C12N 5/078* (2010.01)

(52) U.S. Cl.
CPC ........ *C12N 5/0644* (2013.01); *B01D 2315/02* (2013.01)

(58) Field of Classification Search
CPC ........... B01D 2321/20; B01D 2321/40; B01D 33/08; A61M 1/3496; C12N 5/0641; C12N 5/0644
USPC ........ 210/90, 107, 321.67, 321.68, 636, 741
See application file for complete search history.

(56) References Cited

U.S. PATENT DOCUMENTS

| | | | |
|---|---|---|---|
| 5,194,145 A | | 3/1993 | Schoendorfer |
| 5,762,791 A | * | 6/1998 | Deniega .................. A61M 1/30 210/109 |
| 6,863,821 B2 | * | 3/2005 | Moriarty .................. A61M 1/16 210/321.67 |
| 7,425,265 B2 | * | 9/2008 | Schoendorfer ...... B01D 29/117 210/321.63 |
| 8,840,790 B2 | | 9/2014 | Wegener et al. |
| 2005/0274672 A1 | * | 12/2005 | Tu ....................... A61M 1/3496 210/645 |
| 2012/0095381 A1 | * | 4/2012 | Tonelli .................... A61M 1/16 604/6.09 |
| 2012/0273416 A1 | * | 11/2012 | Wegener ................ B01D 61/22 210/637 |

* cited by examiner

METHOD FOR CONTROLLING FOULING DURING A SPINNING MEMBRANE FILTRATION PROCEDURE

FIELD OF THE DISCLOSURE

The present application is related methods for filtration using separation devices of the type employing relatively rotating surfaces, at least one of which carries a membrane for filtering a supernatant from a cell suspension passed between the surfaces, such as plasma from whole blood or plasma from platelet-rich plasma.

BACKGROUND

There is class of devices that has been used for separating of whole blood into one or more of its constituents, such its cellular constituents (red blood cells and platelets) and its non-cellular constituent (plasma), based on the use of a membrane. More specifically, this type of device employs relatively rotating surfaces, at least one or which carries a porous membrane. Typically the device employs an outer stationary housing and an internal spinning rotor covered by a porous membrane.

One such well-known plasmapheresis device is the Autopheresis-C® separator available from Fenwal, Inc., a Fresenius Kabi company, of Lake Zurich, Ill. A detailed description of a spinning membrane separator may be found in U.S. Pat. No. 5,194,145 to Schoendorfer, which is incorporated by reference herein. This patent describes a membrane-covered spinner having an interior collection system disposed within a stationary shell. Blood is fed into an annular space or gap between the spinner and the shell. The blood moves along the longitudinal axis of the shell toward an exit region, with plasma passing through the membrane and out of the shell into a collection bag. The remaining blood components, primarily red blood cells, platelets and white cells, move to the exit region between the spinner and the shell and then are typically returned to the donor.

Spinning membrane separators have been found to provide improved filtration rates, due primarily to the unique flow patterns ("Taylor vortices") induced in the gap between the spinning membrane and the shell. The Taylor vortices create shear forces in the gap that help to keep the cells, proteins or various biomolecules present in a biological fluid from depositing on and fouling or clogging the membrane.

When a membrane becomes fouled, the effective surface area of the membrane available for filtration is decreased. As membrane surface area decreases the separation efficiency of the device is reduced, and a higher transmembrane pressure (TMP) is required for filtration. It is often desired to prevent, or at least limit, fouling of a membrane. Some degree of fouling is acceptable, as it is representative of an aggressive filtration procedure. However, excessive fouling is indicative of over-aggressive filtration that will lead to pressure and efficiency related issues.

In order to control fouling, the controllers for the separation systems have been programmed with algorithms that monitor the fouling, which is measured as a change in the TMP over time. Monitoring the fouling rate (mmHg/min) provides the system with the information required to make a decision regarding the filtration procedure parameters that aims to reduce fouling in order to maintain fouling rates within predetermined limits.

U.S. Pat. No. 8,840,790, incorporated herein by reference and having the same assignee as the present application, discloses a method for controlling fouling which involves changing the outlet cellular concentration, and in turn the flow rate through the membrane, to control the risk of fouling. For a constant rotation rate and inlet flow rate to the spinner, controlling fouling by changing the outlet concentration directly impacts separation efficiency, with lower outlet concentrations leading to lower efficiencies (efficiency being characterized by the volume of supernatant filtered through the membrane from the cell suspension compared to the supernatant volume entering the spinner). Therefore, current practice, as exemplified by U.S. Pat. No. 8,840,790, can be considered a "variable efficiency" method for controlling fouling.

When the efficiency changes throughout a procedure, via changing the outlet concentration, the overall or averaged concentration of cells flowing out of the spinner can be different for each procedure. During plasmapheresis, in which plasma is separated from red blood cells (RBCs), this is not an issue, as the RBCs that exit the spinner are returned to the donor. Thus, it is not a problem if the concentration of RBCs, (or the hematocrit of the fluid returned to the donor), (and thus the efficiency of the separation) varies slightly throughout the procedure, as it will only affect procedure time. However, in applications that use the cells exiting the spinner as a product, it may be important to maintain a constant concentration (efficiency) throughout a procedure to ensure the products from procedure to procedure contain constant concentrations and volumes. Thus, there is a need for a "constant efficiency" method for controlling fouling of membrane separators during the separation of biological suspensions. The subject matter disclosed herein provides such a "constant efficiency" method.

SUMMARY OF THE DISCLOSURE

The present subject matter has a number of aspects which may be used in various combinations, and the disclosure of one or more specific embodiments is for the purpose of disclosure and description, and not limitation. This summary highlights only a few of the aspects of this subject matter, and additional aspects are disclosed in the drawings and the more detailed description that follows.

The methods of the present disclosure control a spinning membrane separator so as to limit fouling of the membrane by changing the rotation rate of the spinning membrane in response to the fouling rate (i.e., the rate of change of the TMP over time), while maintaining a constant outlet cellular concentration (efficiency). Changing the membrane rotation rate will change the strength of the Taylor vortices, which are responsible for aiding in the prevention of cells from contacting and clogging/fouling the membrane. More specifically, increasing the spinner rotation rate will increase the strength of the Taylor vortices, which should reduce fouling of the membrane. The goal of the method is to rotate the spinning membrane at the slowest rate possible without unacceptable fouling.

Two specific methods to control fouling are disclosed. In a first, "unidirectional" method, the spin rate of the membrane is only increased in response to undesirable fouling in order to prevent the fouling from continuing. In a second, "bidirectional" method, the spin rate of the membrane may be either increased or decreased in response to the measured fouling rate in order to maintain the fouling rate within a desired range. Either or both of the unidirectional and bidirectional methods could be preprogrammed into the programmable controller. If both methods are preprogrammed into the controller, then the operator may select the desired method at the start of the procedure.

In the unidirectional method, the spin rate of the membrane is only increased in response to undesirable fouling. The first method comprises setting an initial spin rate; operating the spinning membrane at the initial spin rate; flowing bulk fluid through the spinning membrane; measuring a fouling rate (FR) corresponding to a change in transmembrane pressure over time ($\Delta TMP/\Delta T$); and comparing the FR to a predetermined maximum fouling rate ($FR_{MAX}$). If FR is greater than (>) $FR_{MAX}$, then a cumulative time above limit during which the FR has been greater than (>) $FR_{MAX}$ (TAL) is determined. If TAL is greater than (>) a predetermined time limit, the spin rate is increased by a predetermined value. Then, a predetermined time is allowed to elapse to permit the TMP to stabilize. The steps are then repeated, beginning with the steps of measuring the fouling rate FR and comparing the FR to a predetermined maximum fouling rate ($FR_{MAX}$).

The initial spin rate corresponds to the lowest spin rate that permits filtration to be maintained at a fouling rate (FR) less than that corresponding to the predetermined maximum fouling rate ($FR_{MAX}$).

In the bidirectional method, the spin rate of the membrane may be both increased and/or decreased in response to a measured fouling rate to maintain the rate of fouling within a desired range. In common with the unidirectional method, the bidirectional method comprises setting an initial spin rate; operating the spinning membrane at the initial spin rate; flowing bulk fluid through the spinning membrane; and measuring a fouling rate (FR) corresponding to a change in transmembrane pressure over time ($\Delta TMP/\Delta T$).

Then, the bidirectional method uniquely requires that the FR be compared to a predetermined maximum fouling rate ($FR_{MAX}$) and a predetermined minimum fouling rate ($FR_{MIN}$). If FR is greater than (>) $FR_{MAX}$, then a cumulative time above limit during which the FR has been greater than (>) $FR_{MAX}$ (TAL) is determined. If FR is less than (<) $FR_{MIN}$, then a cumulative time below limit during which the FR has been less than (<) $FR_{MIN}$ (TBL) is determined. Then, a total cumulative time ($T_{CUM}$) is determined by subtracting TBL from TAL. The $T_{CUM}$ is compared to a negative time limit ($TL_{NEG}$) and a positive time limit ($TL_{POS}$). If $T_{CUM}$ is less than (<) $TL_{NEG}$, then the spin rate is decreased by first preset value. If $T_{CUM}$ is greater than (>) $TL_{POS}$, then the spin rate is increased by a second present value.

Common with the unidirectional method, a predetermined time is then allowed to elapse to permit the TMP to stabilize. Then the steps are repeated, beginning with measuring the fouling rate FR and comparing it to the predetermined maximum fouling rate ($FR_{MAX}$) and the predetermined minimum fouling rate ($FR_{MIN}$). In the bidirectional method, the initial spin rate is between a lower limit that permits filtration to be maintained at an FR less than that corresponding to $FR_{MAX}$, and an upper limit at which the spin rate is below the rate at which known cell damage will occur. Further, the first preset value for decreasing the spin rate may be of the same magnitude as the second preset value for increasing the spin rate.

DETAILED DESCRIPTION

A more detailed description of a system and methods in accordance with the present disclosure is set forth below. It should be understood that the description below is intended to be exemplary, and not exhaustive of all possible variations or applications. Thus, the scope of the disclosure is not intended to be limiting, and should be understood to encompass variations or embodiments that would occur to persons of ordinary skill.

Figure 1:
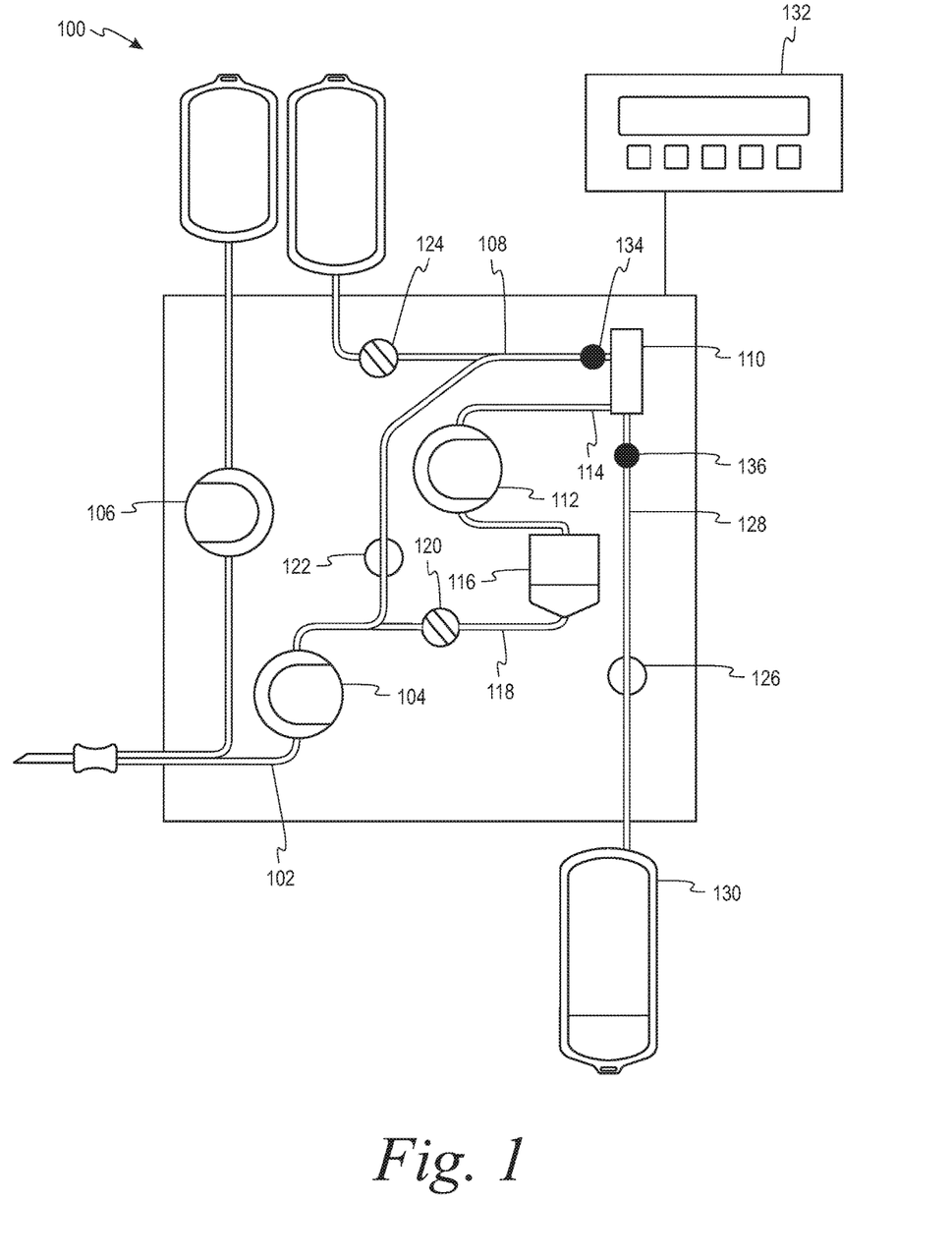
FIG. 1 is a schematic representation of a spinning membrane filtration system with which the methods described herein may be implemented.

The systems and methods of the present application may be advantageously implemented in various procedures in which a suspension of biological cells is separated into its constituents, such as in the separation or concentration of any of red blood cells, platelets, and plasma from whole blood or a blood product. FIG. 1 depicts a spinning membrane separation system 100 that may be used in a plasmapheresis procedure, in which whole blood is separated into plasma and its cellular components. The plasmapheresis procedure is described for illustrative purposes only, and it is understood that the methods for controlling fouling described herein would have applicability in a wide range of apheresis, concentration, washing and mixing procedures.

The system 100 includes a donor line 102 which is acted on by a blood pump 104. Anticoagulant may be added to the whole blood in the donor line 102 by means of a second pump 106. The donor line 102 connects to a processing line 108 for introducing anticoagulated whole blood into the inlet of a spinning membrane separator 110. A third pump 112 acts on a first outlet line 114 to flow separated red blood cells (the retentate in a plasmapheresis procedure) to an in-process reservoir 116, which is connected by way of return line 118 to the donor line for the return of the separated RBCs to the donor. A plasma line 128 is connected to a second outlet of the separator 110 for flowing separated plasma (the filtrate in a plasmapheresis procedure to a plasma collection container 130. Flow through the several lines is selectively controlled by operation of the clamps 120, 122, 124 and 126. The operation of the pumps 104, 106, 112, the clamps 120, 122, 124, 126, and the speed of rotation of the spinning membrane are automatically controlled by a programmable controller 132. The controller 132 may be preprogrammed to operate the system 100 in accordance with a number of different separation protocols, and includes a keypad to permit the operator to input information into the controller.

Figure 2:
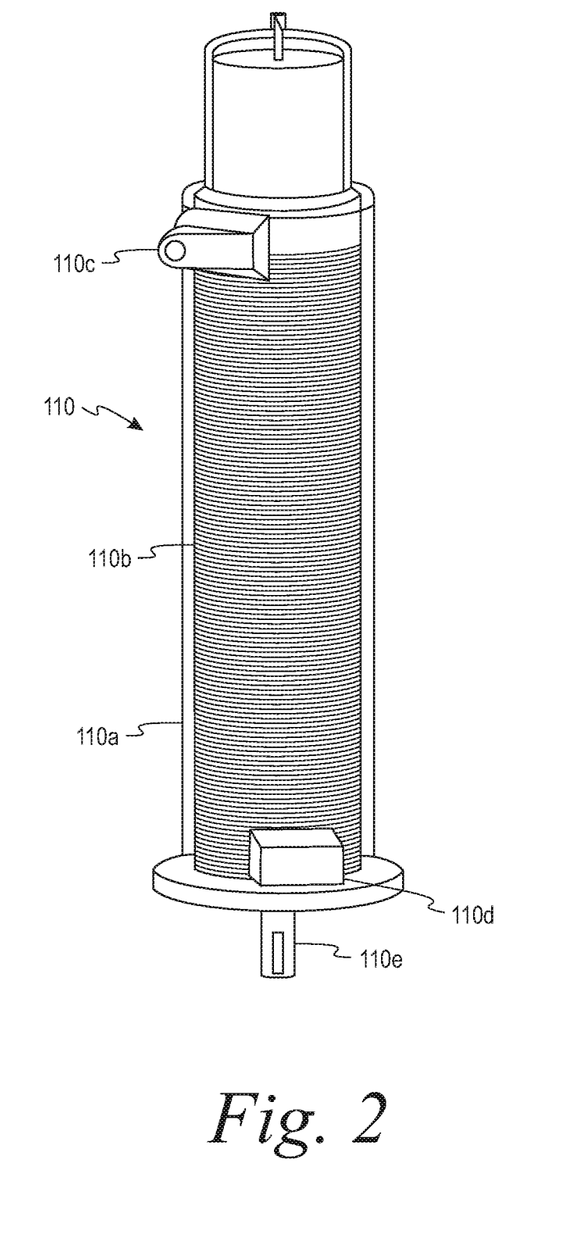
FIG. 2 is a schematic representation of a spinning membrane separator suitable for use in the system of FIG. 1, with portions shown in ghost line to show interior detail.

With reference to FIG. 2, the spinning membrane separator 110 comprises a housing 110a, with a rotary spinner 110b mounted for relative rotation within the housing 110 and having a filter membrane on the surface thereof. The housing 110a further includes an inlet 110c in fluid communication with the processing line 108, a first outlet 110d in fluid communication with the outlet line 114, and a second outlet 110e in fluid communication with the plasma line 128. Pressure sensors 134, 136 are associated with the processing line 108, adjacent the inlet 110c, and the plasma line 128, adjacent the second outlet 110e, for providing signals to the controller 132 by which the transmembrane pressure is determined.

During the plasmapheresis procedure, membrane fouling may occur in which cellular materials are deposited on the surface of the spinning membrane, thus increasing the resistance of the membrane to fluid flow. By way of the present disclosure fouling of the membrane is controlled by adjusting the spin rate of the membrane in response to changes in the transmembrane pressure.

In the first, unidirectional method, where the spin rate is only increased in response to the undesirable fouling in an attempt to prevent the fouling from continuing, the spinning membrane is rotated at the start of the procedure at lowest spin rate that is empirically known to be just above the rate at which filtration cannot be maintained without extreme fouling (i.e., the shear forces from Taylor vortex flow are too weak to sweep the membrane surface). The goal is to spin the membrane as slowly as possible. Thus, an initial spin rate near or at the lower limit is an aggressive way to start a procedure. Ideally, the system would stay at this spin rate for the duration of the procedure, but if fouling occurs the spin rate will be increased (to increase the shear forces from the Taylor vortices) to reduce the risk fouling.

Accordingly, the fouling rate of the membrane, i.e., the change in pressure over time, is measured. The fouling rate may be measured as disclosed in U.S. Pat. No. 8,840,790. If the fouling rate is less than a preset maximum limit, then the current spin rate is continued. If the fouling rate is greater than a preset maximum limit, then the amount of time the fouling rate is above the fouling limit is added to a rolling sum that tracks the time that the fouling has been above the maximum limit. The time at which the fouling rate is above the maximum limit is measured for a specific period of time before a decision is made to change (increase) the spin rate in order to reduce the likelihood of changing the spin rate in response to noise.

As long as the rolling sum, tracking the time the fouling rate has been greater than the maximum limit, is less than a preset allowed amount of time, then the spinning membrane separator continues to operate at the current spin rate. The maximum time limit can be determined experimentally, and will be dependent upon the application. A maximum time limit of from 10 seconds to 30 seconds is anticipated.

Once the rolling sum, tracking the time the fouling rate has been greater than the limit, is greater than a preset allowed period of time, the spin rate of the separator is then increased by a preset amount. After increasing the spin rate, a specific amount of time is allowed to pass to permit the transient pressure response from spin rate change to stabilize. Specifically, the spinner rotation creates a centrifugal pressure that is dependent on the spin rate. Thus, when changing the spin rate a transient pressure change will occur. After the transmembrane pressure stabilizes, the steps described above are repeated, beginning with the measurement of the fouling rate.

Figure 3:
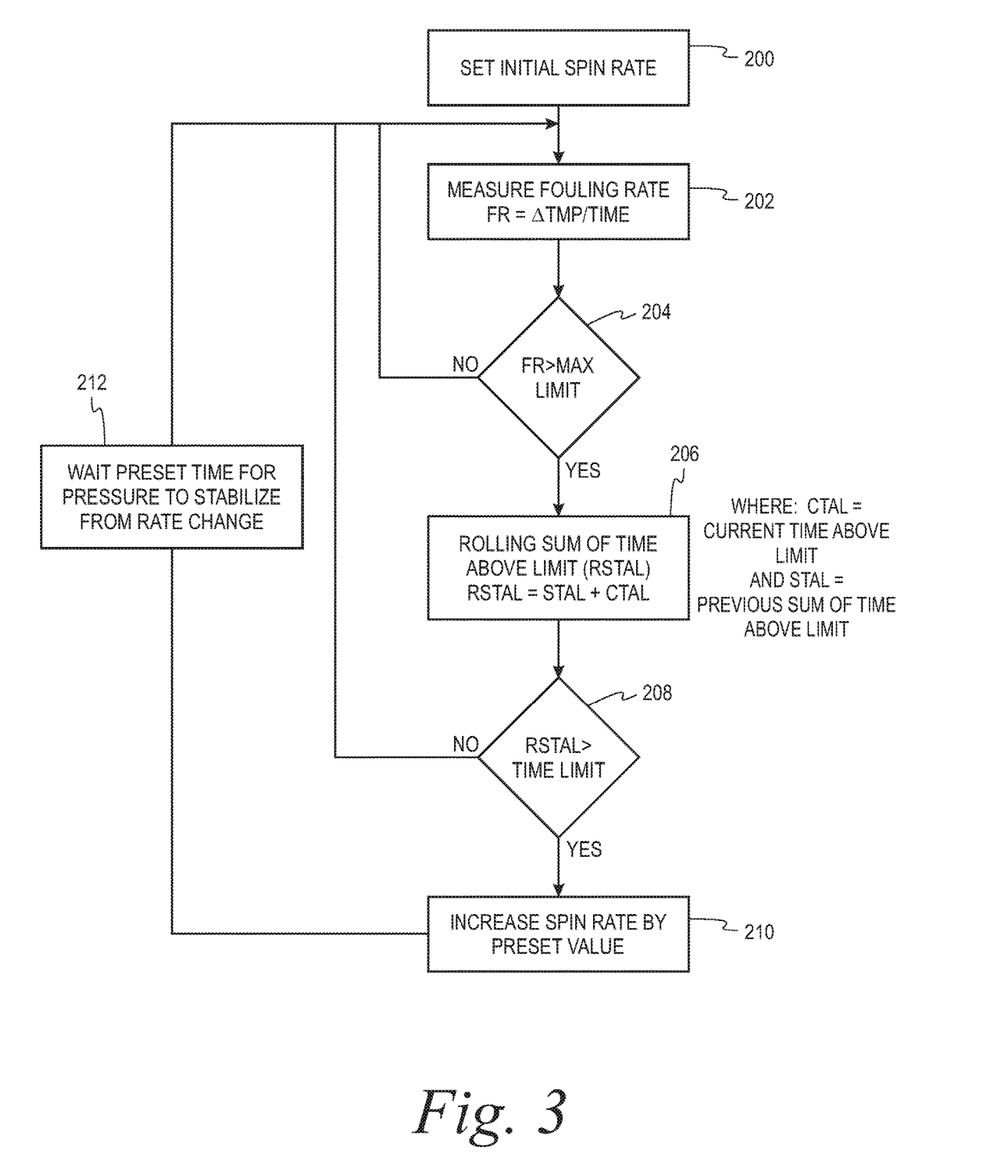
FIG. 3 is a flow chart showing the steps of a "unidirectional" method for controlling the operation of a spinning membrane separator to control fouling, in which the rotational speed of the spinning membrane is only increased in response to an unacceptable rate of fouling.

With reference to FIG. 3, a flow chart setting forth the steps of the unidirectional method for controlling the operation of a spinning membrane separator to control fouling is seen. The unidirectional method comprises setting an initial spin rate (Box 200), as either input into the controller by the operator, or preprogrammed into the controller based on the type of separation procedure being performed. The spinning membrane is then operated at the initial spin rate. As noted above, the initial spin rate preferably corresponds to the lowest spin rate, empirically determined beforehand, that permits filtration to be maintained at a fouling rate (FR) less than that corresponding to the predetermined maximum fouling rate ($FR_{MAX}$).

The unidirectional method proceeds with flowing bulk fluid (e.g., whole blood) through the spinning membrane by means of pump 104, with the clamp 120 being open, both as controlled by the controller. Then, the fouling rate (FR), corresponding to a change in transmembrane pressure over time ($\Delta TMP/\Delta T$), is measured (Box 202) by the controller 132 based on the signals received from the pressure sensors 134, 136. FR is then compared to a predetermined maximum fouling rate ($FR_{MAX}$), or "Max limit" (Box 204).

If FR is greater than (>) $FR_{MAX}$, then a cumulative time, or rolling sum of the time, above the limit during which the FR has been greater than (>) $FR_{MAX}$ (STAL) is determined by the controller 132. See, Box 206—"Rolling SUM of Time Above Limit (RSTAL)=STAL+CTAL, where CTAL=Current Time Above Limit and STAL=Previous Sum of Time Above limit. If RSTAL is greater than (>) a predetermined time limit (Box 208), then the controller 132 increases the spin rate by a preset or predetermined value (Box 210). Then, a predetermined time is allowed to elapse to permit the TMP to stabilize (Box 212). The steps are then repeated, beginning with the steps of measuring the fouling rate FR and comparing the FR to a predetermined maximum fouling rate ($FR_{MAX}$) (returning to Box 202).

If upon measuring FR (Box 202), it is less than (<) $FR_{MAX}$, then the controller 132 continues to measure the FR until such time that it is greater than (>) $FR_{MAX}$. If the cumulative time (RSTAL) is less than (<) the predetermined time limit (Box 206), the spin rate of the membrane remains unchanged, and FR continues to be measured by the controller 132 (returning to Box 202) until such time that the cumulative time (RSTAL) is greater than the predetermined time limit. Then the controller 132 will increase the spin rate as described above. The system continues to be operated in accordance with the steps described above until the completion of the separation procedure.

In the bidirectional method, where the spin rate may be either increased or decreased in response to the measured fouling rate in order to maintain a fouling rate within a desire range, the spin rate applied at the start of the procedure is that which is within the empirically known limits of a particular application or procedure. The lower limit is the spin rate just above the point at which it is known filtration cannot be maintained without extreme fouling (i.e., the shear forces from Taylor vortex flow are too weak to sweep the membrane surface of cellular material), while the upper limit is the rate just below the point at which it is known that cell damage will occur (i.e., the shear forces from Taylor vortex flow are too strong).

Like the unidirectional method, the fouling rate of the membrane, i.e., the change in pressure over time, is measured. However, in the bidirectional method, the fouling rate is tracked whenever it is determined to be above a maximum limit, or below a minimum limit, with the net amount of time being considered before making a decision to change the spin rate. The basic premise is, if the fouling rate is too high, the spin rate is increased to prevent additional fouling; if the fouling rate is too low, then the spin rate is decreased closer to the point where fouling may occur, thus reducing the shear forces to which the cells are subjected to reduce the likelihood of cellular damage.

In the bidirectional method, if the fouling rate is both less than a preset maximum limit and greater than a preset minimum limit, the current spin rate continues to be applied. If the fouling rate is greater than the preset maximum limit, then the amount of time the fouling rate is above the limit is added to a rolling sum that tracks the cumulative time the fouling rate is outside either the minimum or maximum limits. If the fouling rate is less than the preset minimum limit, then the amount of time the fouling rate is below the limit is subtracted from the rolling sum.

For example, if the fouling rate is above the maximum limit for 1 second, followed by a fouling rate in between the minimum and maximum limits for 1 second, followed by a fouling rate below the minimum limit for 1 second, the net rolling sum or cumulative time would be equal to 0 seconds, as the 1 second above the max limit and the 1 second below the min limit cancel each other. Consequently, the rolling sum will be positive if the fouling rate is above the maximum limit for an extended period of time, and negative if the fouling rate is below the minimum limit for an extended period of time.

As long as the rolling sum for the time is in between positive and negative time limits, then the current spin rate continues to be applied. However, if the rolling sum is greater than the positive time limit, representing fouling above the maximum fouling limit for an extended period of time, then the spin rate is increased by a preset amount. If the rolling sum is less than the negative time limit, representing fouling below the minimum fouling limit for an extended period of time, then the spin rate is decreased by a preset amount.

Then, like the unidirectional method, a specific amount of time is allowed to pass to permit the transient pressure response from spin rate change to stabilize. After the transmembrane pressure stabilizes, the steps described above are repeated, beginning with the measurement of the fouling rate, until the completion of the separation procedure.

Figure 4:
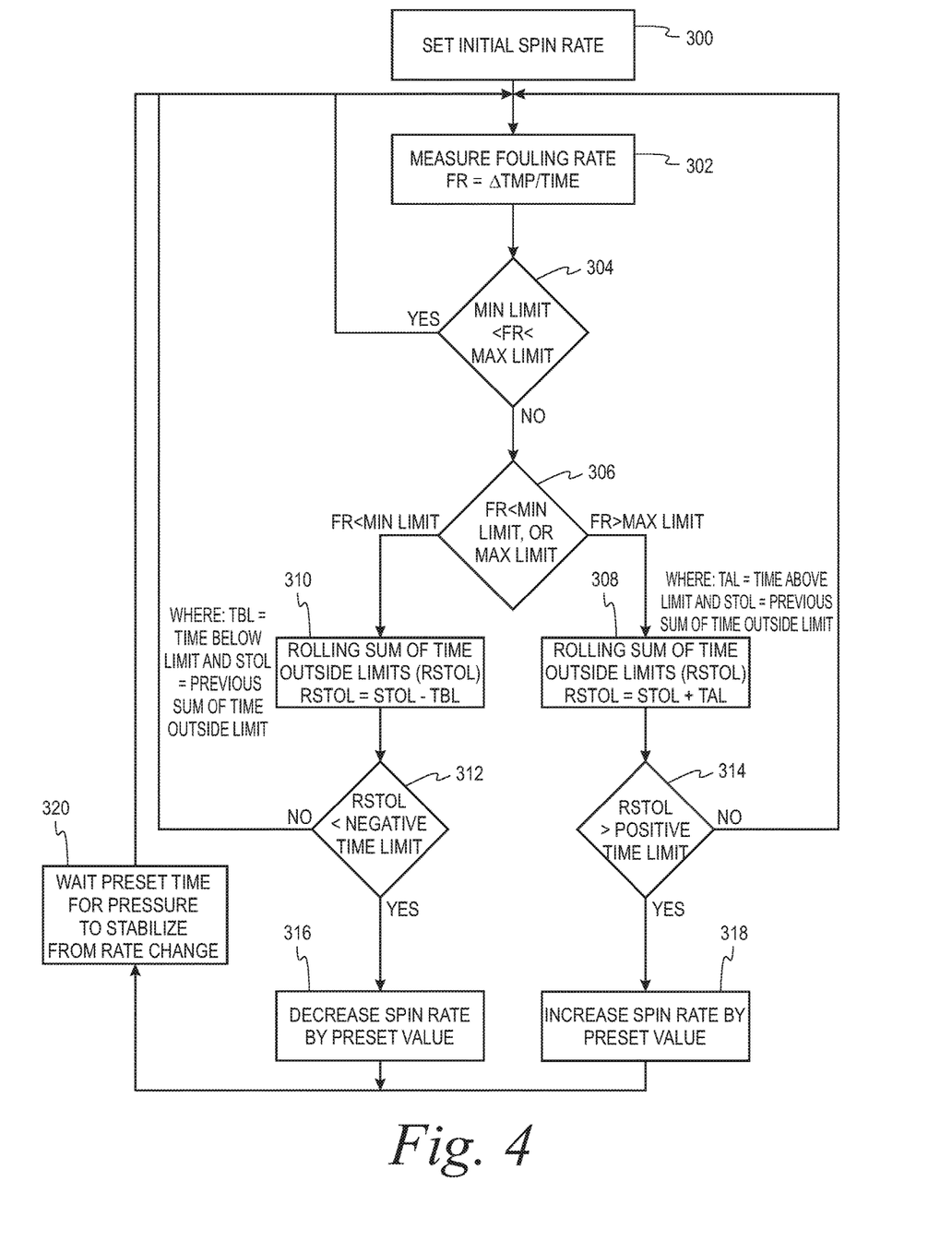
FIG. 4 is a flow chart showing the steps of a "bidirectional" method for controlling the operation of a spinning membrane separator to control fouling, in which the rotational speed of the spinning membrane may be both increased and/or decreased in response to the measured rate of fouling in order to maintain the rate of fouling within a desired range.

With reference to FIG. 4, a flow chart setting forth the steps of the bidirectional method for controlling the operation of a spinning membrane separator to control fouling is seen. In common with the unidirectional method, the bidirectional method comprises setting an initial spin rate (Box 300), as either input into the controller by the operator or preprogrammed into the controller. Then the spinning membrane is operated at the initial spin rate by the controller 132. As noted above, the initial spin rate preferably is that which is within the empirically-known limits of a particular application or procedure, with the lower limit being the spin rate just above the point at which it is known filtration cannot be maintained without extreme fouling, and the upper limit being the rate just below the point at which it is known that cell damage will occur.

The bidirectional method proceeds with the controller 132 operating the pump 104 to flow bulk fluid (e.g., whole blood) through the spinning membrane. Then, the controller 132 measures the fouling rate (FR), corresponding to a change in transmembrane pressure over time ($\Delta TMP/\Delta T$) (Box 302) based on signals received from the pressure sensors 134, 136. FR is then compared by the controller 132 to the predetermined maximum fouling rate ($FR_{MAX}$) and the predetermined minimum fouling rate ($FR_{MIN}$). If FR is between the predetermined minimum and maximum fouling rates (Box 304—"Min limit<FR<Max limit"), then the controller 132 continues to measure the FR, and there is no change in the spin rate.

If the controller 132 determines that FR is either less than $FR_{MIN}$ or greater than (>) $FR_{MAX}$ (Box 306), then one of two paths is taken by the controller 132 to calculate a cumulative or Rolling Sum of Total Time Outside Limits (RSTOL). If FR is greater than (>) $FR_{MAX}$, then the current time during which FR has been greater than (>) $FR_{MAX}$ (TAL) is added to the previous sum of time outside limit (STOL) to obtain the RSTOL (Box 308). If FR is less than (<) $FR_{MIN}$, then the current time during which the FR has been less than (<) $FR_{MIN}$ (TBL) is subtracted from STOL to obtain the RSTOL (Box 310). In other words, the total cumulative time outside the limit (RSTOL) is determined by subtracting TBL from TAL.

The controller 132 then compares RSTOL to a negative time limit ($TL_{NEG}$) (Box 312) and a positive time limit ($TL_{POS}$) (Box 314). If RSTOL is less than (<) $TL_{NEG}$, then the controller 132 decreases the spin rate by a first preset value (Box 316). If RSTOL is greater than (>) $TL_{POS}$, then the controller 132 increases the spin rate by a second preset value (Box 318). If RSTOL is neither less than (<) $TL_{NEG}$ nor greater than (>) $TL_{POS}$, then FR continues to be measured by the controller 132, and there is no change in the spin rate (return back to Box 302).

If the spin rate is either decreased (Box 316) or increased (Box 318) by the controller 132, then, common with the unidirectional method, a predetermined time is allowed to elapse to permit the TMP to stabilize (Box 320). Then the steps are repeated, beginning with measuring the fouling rate FR (Box 302) and comparing it to the predetermined maximum fouling rate ($FR_{MAX}$) and the predetermined minimum fouling rate ($FR_{MIN}$) (Box 304).

Figure 5:
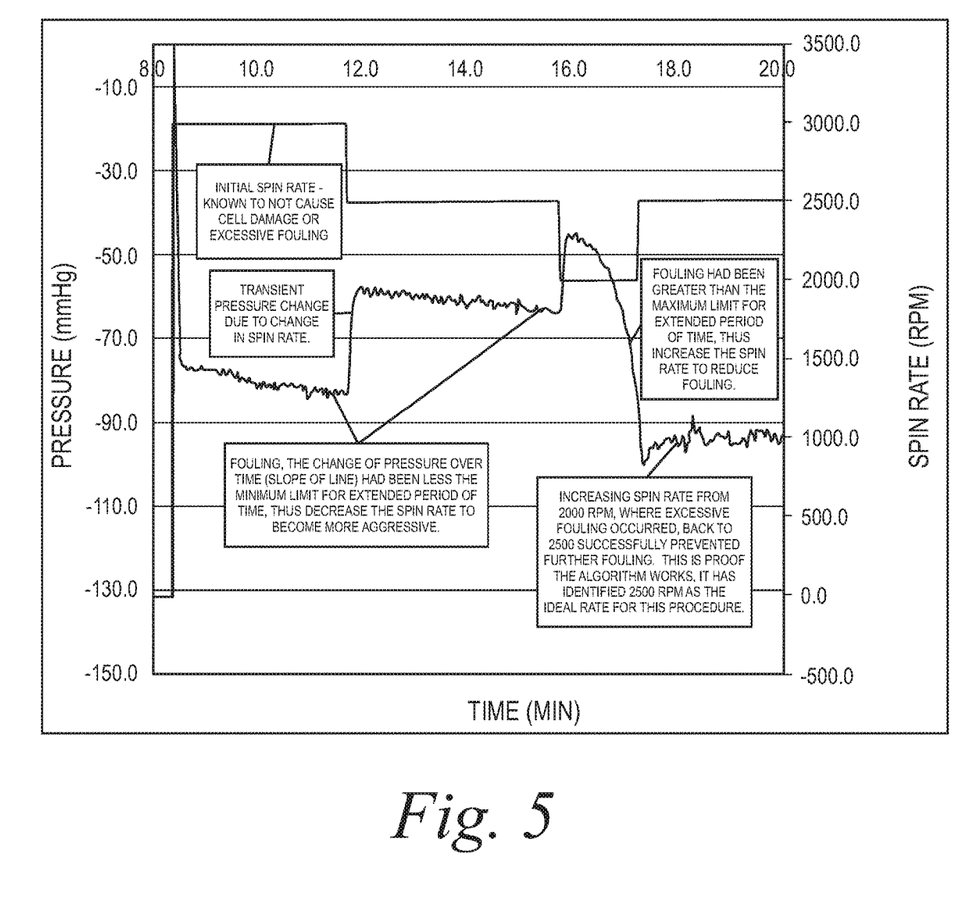
FIG. 5 is a plot of an exemplary procedure using the "bidirectional" method of FIG. 4 to control fouling of the membrane, in which the vertical axis represents both the pressure drop (in mmHg) across the membrane and the spin rate (in RPM) of the membrane, while the horizontal axis represents the time (in minutes) of the procedure.

With reference to FIG. 5, a plot of an exemplary procedure using the bidirectional method of FIG. 4 to control fouling of the membrane in the context of a platelet concentration (or washing) procedure. In FIG. 5, the left-hand vertical axis represents the pressure drop (in mmHg) across the membrane, while the right-hand vertical axis represents the spin rate (in RPM) of the membrane. The horizontal axis represents the time (in minutes) of the procedure.

Upon the start of the procedure (indicated as minute 8.0 on the time axis), the spin rate is increased from 0.0 RPM to 3000.0 RPM. As noted, this initial spin rate is selected as it is known empirically not to cause cell damage or excessive fouling. Simultaneously, the pressure across the membrane decreases from 0.0 mmHg to approximately −75 mmHg.

Between minutes 8.0 and approximately 12.0, the spin rate is maintained at 3000 RPM. However, the pressure drop across the membrane increases, as indicated by the overall slope of the line being negative, thus indicating an increase in the fouling rate (FR) over this time period. However, the fouling rate was such that the cumulative time was below the minimum limit (i.e., FR is less than (<) $FR_{MIN}$, and the cumulative time below limit, $T_{CUM}$, is less than (<) $TL_{NEG}$). Thus, the spin rate is decreased to 2500.0 RPM, and a transient change in the transmembrane pressure to approximately −55 mmHg is experienced.

Between minutes 12.0 and approximately 16.0, the spin rate is maintained at 2500 RPM. Again, the pressure drop across the membrane increases, as indicated by the overall slope of the line being negative, thus indicating an increase in the fouling rate (FR) over this time period. However, the fouling rate again was such that the cumulative time was below the minimum limit, and the spin rate is decreased to 2000.0 RPM.

A transient change in the transmembrane pressure to approximately −45 mmHg is experienced initially. However, the transmembrane pressure quickly drops between minutes 16.0 and 18.0 to approximately −100 mmHg, indicating excessive fouling. The fouling rate was such that the cumulative time was above the maximum limit (i.e., FR is greater than (>) $FR_{MAX}$, and the cumulative time above limit, $T_{CUM}$, is greater than (>) $TL_{POS}$), and the spin rate is increased back to 2500.0 RPM. Between 18.0 and 20.0 minutes, the transmembrane pressure remains relatively constant, indicating that substantially no further fouling has occurred.

In the example, the incremental change in the spin rate of 500 RPM was chosen simply for demonstrative purposes. Smaller incremental changes may be preferable in order to maintain a more stable control of the separation process. Further, the initial spin rate may vary depending on the type of separation procedure being performed.

Thus, an improved method to operating a spinning membrane separator so as to control membrane fouling and produce a consistent cellular product has been provided. The foregoing description is intended to be illustrative, and is not intended to limit the method to any specific application, system or device.

The invention claimed is:

1. A system for separating a suspension of biological cells comprising:
   a) a separator having a membrane rotatably mounted therein;
   b) a first inlet line for flowing the suspension of biological cells into the separator;
   c) a first pressure sensor associated with the first inlet line;
   d) a first outlet line for flowing retentate from the separator;
   e) a second outlet for flowing filtrate from the separator;
   f) a second pressure sensor associated with the second outlet; and
   g) a controller configured to determine the change in pressure across the membrane over time based on signals received from the first and second pressure sensors ($\Delta TMP/\Delta T$) corresponding to a fouling rate (FR), to compare the FR to a predetermined maximum fouling rate $FR_{MAX}$, and to control a spin rate for the membrane in response to the comparison of the fouling rate (FR) to the predetermined maximum fouling rate $FR_{MAX}$.

2. The system of claim 1 wherein the controller is further configured to increase the spin rate of the membrane in response to the FR exceeding a predetermined maximum fouling rate ($FR_{MAX}$).

3. The system of claim 1 wherein the predetermined maximum fouling rate ($FR_{MAX}$) is preprogrammed into the controller.

4. The system of claim 1 wherein the controller is configured to permit an operator to input the predetermined maximum fouling rate ($FR_{MAX}$).

5. The system of claim 1 wherein the controller is configured to increase the spin rate if FR exceeds $FR_{MAX}$ for a predetermined cumulative amount of time.

6. The system of claim 5 wherein the controller is preprogrammed to increase the spin rate by a predetermined amount.

7. The system of claim 5 wherein the controller is configured to permit an operator to input the amount by which the spin rate is to be increased.

8. The system of claim 1 wherein the controller is configured to increase the spin rate of the membrane in response to the FR being greater than a predetermined maximum fouling rate ($FR_{MAX}$) and to decrease the spin rate of the membrane in response to the FR being less than a predetermined minimum fouling rate ($FR_{MIN}$).

9. The system of claim 8 wherein the controller is configured to change the spin rate of the membrane based on a cumulative time, corresponding to the difference in time during which FR is greater than $FR_{MAX}$ and during which FR is less than $FR_{MIN}$, exceeding a predetermined time limit.

10. The system of claim 8 wherein the controller is preprogrammed to change the spin rate by a predetermined amount.

11. The system of claim 8 wherein the controller is configured to receive operator input of an amount by which the spin rate is to be changed.

12. A system or separating a suspension of biological cells comprising:
   a) a separator having a membrane rotatably mounted therein;
   b) a first inlet line for flowing the suspension of biological cells into the separator;
   c) a first pressure sensor associated with the first inlet line;
   d) a first outlet line for flowing retentate from the separator;
   e) a second outlet for flowing filtrate from the separator;
   f) a second pressure sensor associated with the second outlet; and
   g) a controller programmed to sequentially: i) either set an initial spin rate for the spinning membrane or to receive operator input of the initial spin rate; ii) operate the spinning membrane at the initial spin rate; iii) flow bulk fluid through the spinning membrane; iv) measure a fouling rate (FR) corresponding to a change in transmembrane pressure over time ($\Delta TMP/\Delta T$); v) compare the FR to a predetermined maximum fouling rate ($FR_{MAX}$) and a predetermined minimum fouling rate ($FR_{MIN}$); vi) if $FR>FR_{MAX}$, determine a current time above limit during which the FR has been $>FR_{MAX}$ (TAL); vii) if $FR<FR_{MIN}$, determine a current time below limit during which the FR has been $<FR_{MIN}$ (TBL); viii) determine a total cumulative time outside the limit (RSTOL) by subtracting TBL from TAL; ix) compare RSTOL to a negative and positive time limit ($TL_{NEG}$ and $TL_{POS}$); x) if $RSTOL<TL_{NEG}$, decrease the spin rate by a first preset value; xi) if $RSTOL>TL_{POS}$, increase the spin rate by a second preset value; xii) wait a predetermined time to allow for the TMP to stabilize; and xiii) return to iv).

* * * * *